(12) United States Patent
Anderton et al.

(10) Patent No.: US 7,499,524 B2
(45) Date of Patent: Mar. 3, 2009

(54) METHODS AND APPARATUS FOR MOBILE IMAGING SYSTEMS

(75) Inventors: Richard Larry Anderton, West Jordan, UT (US); Francois Emmanuel Falco, South Jordan, UT (US); David Ellis Barker, Salt Lake City, UT (US); Samuel Lee Alder, Stansbury Park, UT (US)

(73) Assignee: General Electric Company, Schenectady, NY (US)

( * ) Notice: Subject to any disclaimer, the term of this patent is extended or adjusted under 35 U.S.C. 154(b) by 238 days.

(21) Appl. No.: 11/412,590

(22) Filed: Apr. 27, 2006

(65) Prior Publication Data

US 2007/0253540 A1    Nov. 1, 2007

(51) Int. Cl.
*H05G 1/10*       (2006.01)
*H01J 35/12*      (2006.01)
(52) U.S. Cl. .................. 378/101; 378/102; 378/200
(58) Field of Classification Search .............. 378/102, 378/103, 117, 119, 130, 141, 193, 199, 200
See application file for complete search history.

(56) References Cited

U.S. PATENT DOCUMENTS

| 4,053,778 | A | 10/1977 | Franke | 250/402 |
|---|---|---|---|---|
| 4,079,265 | A | 3/1978 | Woodburn | 307/108 |
| 4,080,558 | A | 3/1978 | Sullivan | 320/39 |
| 4,186,329 | A | 1/1980 | Fairbairn | 315/241 |
| 4,321,523 | A | 3/1982 | Hammel | 320/14 |
| 5,017,800 | A | 5/1991 | Divan | 307/66 |
| 5,036,284 | A | 7/1991 | Cichanski | 324/433 |
| 6,118,845 | A | 9/2000 | Simon et al. | 378/62 |
| 6,126,314 | A * | 10/2000 | Morasse | 378/167 |
| 6,370,224 | B1 | 4/2002 | Simon et al. | 378/62 |
| 6,470,207 | B1 | 10/2002 | Simon et al. | 600/426 |
| 6,477,400 | B1 | 11/2002 | Barrick | 600/426 |
| 6,892,090 | B2 | 5/2005 | Verard et al. | 600/424 |
| 6,920,347 | B2 | 7/2005 | Simon et al. | 600/424 |
| 6,947,786 | B2 | 9/2005 | Simon et al. | 600/427 |
| 6,968,224 | B2 | 11/2005 | Kessman et al. | 600/407 |
| 7,016,467 | B2 * | 3/2006 | Brooks | 378/102 |
| 2002/0191744 | A1 * | 12/2002 | Mirabella | 378/102 |
| 2005/0117706 | A1 * | 6/2005 | Powell | 378/141 |
| 2007/0269010 | A1 * | 11/2007 | Turner | 378/102 |

* cited by examiner

*Primary Examiner*—Irakli Kiknadze
(74) *Attorney, Agent, or Firm*—Fisher Patent Group, LLC; Thomas M. Fisher

(57) ABSTRACT

A system for reconstructing an image of an object includes a mobile imaging system, and a user removable module configured to be attached to the mobile imaging system.

16 Claims, 1 Drawing Sheet

METHODS AND APPARATUS FOR MOBILE IMAGING SYSTEMS

BACKGROUND OF THE INVENTION

This invention relates generally to methods and apparatus for computed tomography (CT), and more particularly to methods and apparatus that facilitate prolonged imaging with mobile medical imaging equipment.

Cardiovascular Imaging and/or Interventional Vascular imaging places heavy x-ray power and cooling demands on the x-ray tube during operation. Most systems are "fixed" or stationary systems, thus have permanent heavy duty wiring along with heat exchangers and cooling lines to remote locations where large quantities of heat can be dissipated. Additionally, with stationary systems, the typical power provided is more than the 110 volt 15-30 amp circuit typically found in a common outlet. The advent of mobile C-arm systems has placed heavy demands on power availability from common electrical outlets, and the cooling requirements for the x-ray tube of the mobile system. This has resulted in the need to carefully manage procedures in order to stay within the operating capability of mobile C-arm fluoroscopic equipment.

Also, dose reduction is an increasingly demanding challenge, and drives the need to use greater x-ray beam filtration to increase the imaging effectiveness of the x-ray beam. This further increases the power requirements for imaging, and increases the cooling demands for the x-ray tube and generator system. It would therefore be desirable to increase the available cooling and available power in mobile C-arm fluoroscopic equipment.

BRIEF DESCRIPTION OF THE INVENTION

In one aspect, a system for reconstructing an image of an object is provided. The system includes a mobile imaging system, and a user removable module configured to be attached to the mobile imaging system.

In another aspect, a method of alerting a user of a need for replacing a spent user removable module with a fresh user removable module is provided. The method includes monitoring a temperature of a cooling fluid in a user removable module along with the computed state of the eutectic material, monitoring a charge level of a module battery in the user removable module, and alerting the user when at least one of the temperature, eutectic status, and the charge level is indicative of a replacement module need.

In still another aspect, a method of imaging a patient is provided. The method includes imaging with a mobile imaging system including a first user removable module, stopping the imaging, removing the first user removable module, installing a second user removable module, and restarting the imaging.

In yet another aspect, a method of augmenting the capacity of an imaging system is provided. The method includes plugging a mobile imaging system into a standard outlet, wherein the mobile imaging system has a system battery and a capacitor bank such that the system is able to use more power at peak periods than is provided from the outlet, wherein the mobile imaging system's peak power is P1, and coupling a user removable module to the mobile imaging system such that at least one of the following is provided by the user removable module: an additional cooling capacity; an ability to provide P1 more often; and an additional x-ray power in addition to P1.

DETAILED DESCRIPTION OF THE INVENTION

There are herein provided methods and apparatus useful for imaging systems such as, for example, but not limited to a Fluoroscopy System and a Computed Tomography (CT) System with a Fluoroscopy mode (CT fluoroscopy). The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 1:
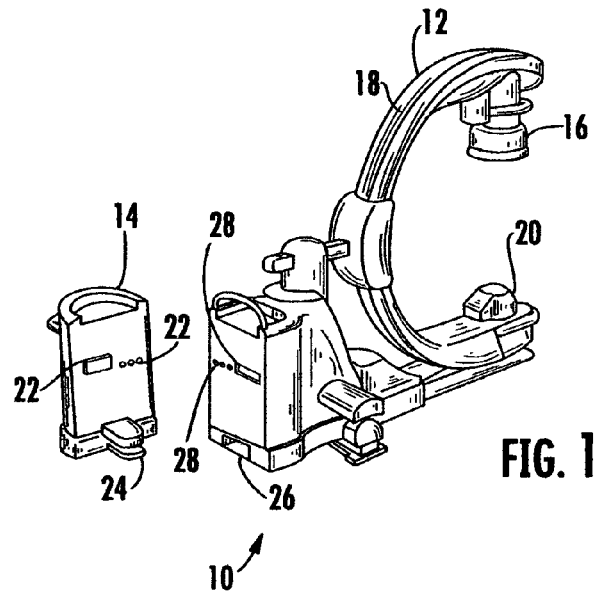
FIG. 1 is a pictorial view of a mobile imaging docking system.
Figure 2:
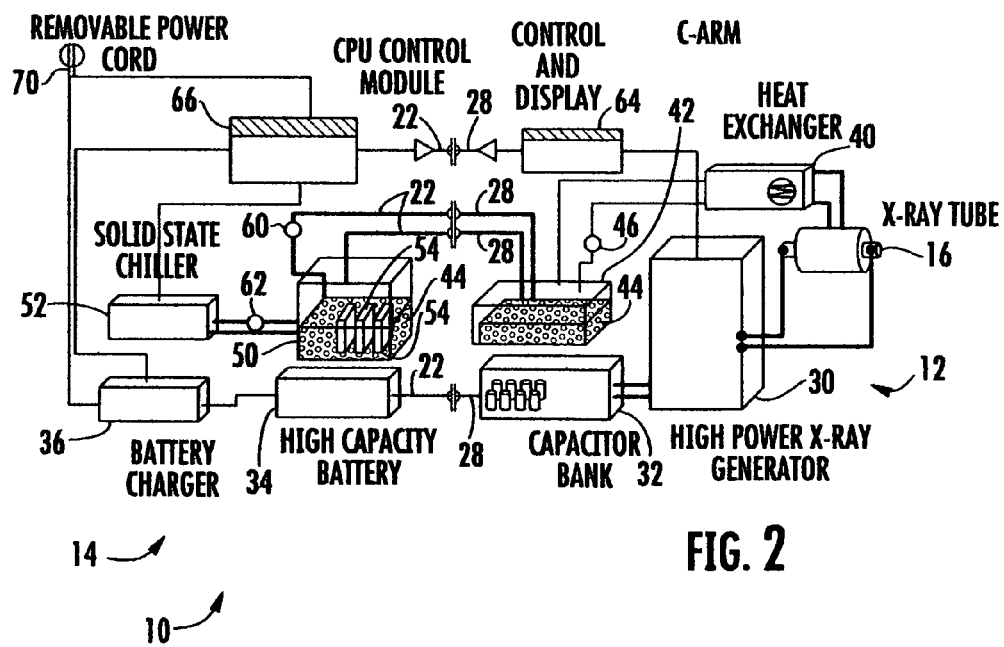
FIG. 2 is a block schematic diagram of the system illustrated in FIG. 1.

FIG. 1 is a pictorial view of an x-ray image mobile modular system 10. FIG. 2 is a block schematic diagram of system 10 illustrated in FIG. 1. In the exemplary embodiment, system 10 includes a mobile imaging system 12 and a user removable module 14. The user removable module is attachable and removable by hospital or other facility employee and is also referred to herein as a dockable module, and system 10 is also referred to as a docking module system. As illustrated in FIG. 1, system 12 can be a C-arm fluoroscopy imaging system. However, it is contemplated that the benefits of the invention accrue to other types of mobile x-ray systems, and therefore system 12 can be a non-C-arm gantry type CT system with or without Fluoroscopic capabilities. As used herein the terms imaging and imaging procedure include a mechanical 3D scan.

System 12 includes a radiation source 16 on one end of a C-arm 18 and a radiation detector 20 on an opposite end of C-arm 18. A plurality of connectors 22 are on user removable module 14. A mechanical guide extension 24 extends from a base portion of user removable module 14 and mates with a corresponding receptacle 26 on system 12. Additionally, a plurality of connectors 28 are on system 12.

FIG. 2 illustrates schematically the connectors 22 and 28, and the interfacing of system 12 with user removable module 14. System 12 includes a high power x-ray generator 30 coupled to the radiation source 16 such as an x-ray tube 16. High power generator 30 is coupled to a standard 110 volt outlet and to a capacitor bank 32 that provides additional power over the power provided by the outlet. Capacitor bank 32 is powered by a battery in system 12 (not shown) in accordance with U.S. Pat. No. Re. 35,025. Accordingly, system 12 can provide higher power operations than a mobile C-arm Fluoroscopy system without a capacitor bank and battery.

Through use of system 12, the capacitor bank 32 discharges and loses energy, and the battery in system 12 (system battery) recharges the capacitor bank 32 as is described in Re. 35,025. However, system 10 includes user removable module 14 that includes a high capacity battery 34, and when module 14 is coupled with system 12 as illustrated schematically in FIG. 2, module 14 augments the power supplied provided by the system battery in system 12 and the power from the standard 110 volt outlet that system 12 is plugged into. User removable module 14 includes a battery charger 36 that charges battery 34. Also, through use of system 12, heat is generated by x-ray tube 16 which is coupled to a heat exchanger 40 that is coupled to a reservoir 42.

A coolant 44 (cooling liquid) such as antifreeze (propylene glycol in water) is pumped from reservoir 42 through heat exchanger 40 by a pump 46. Of course, other cooling liquids can be used. Through use of system 12, coolant 44 is heated. Therefore, user removable module 14 also includes a reservoir 50 holding coolant 44. Reservoir 50 is coupled to a solid state chiller 52 that removes heat from a plurality of cooling modules 54 during the recharge process of the user removable module. The cooling modules 54 contain a eutectic material that removes heat from coolant 44 when user removable module is attached to system 12 during normal operations. As explained below, after being used, user removable module can be removed from system 23 and during the recharge process, a pump 62 delivers the coolant from chiller 52 to modules 54 to cool the eutectic material therein in order to freeze the material.

Both user removable module 14 and system 12 include a computer or controller to communicate to each other when coupled. In system 12, a computer 64 controls the image acquisition and displays the image. In user removable module 14, a computer 66 controls the operations of the battery charger 36 and the solid state chiller 52. In one embodiment, one of computer 64 and/or computer 66 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits. In one embodiment, user removable module 14 includes a removable power cord 70 which can be removed to increase the mobility and aesthetics of module 14.

In order to inform a user of the need to replace one user removable module 14 with another user removable module 14, one embodiment monitors the charge of battery 34 and the temperature of coolant 44 and alerts the user that a replacement user removable module 14 is needed, or will be needed within a certain time. For example, one embodiment provides a half hour warning to allow a surgeon to arrive at a convenient stopping point before user removable module 14 is removed. Additionally, the half hour (or other time period, which in one embodiment is user selectable) allows for retrieval from a possibly remote location of a fresh module 14 to replace the spent module 14. Depending on how many user removable modules 14 the facility has, the facility can wait for the first user removable module 14 to be recharged or the facility can restart the imaging with a second fresh user removable module 14. In addition to the above status monitoring, one embodiment employs the monitoring as a maintenance aid. For example, when either the temperature of the coolant rises faster than a preprogrammed rate or the battery 34 discharges faster than a preprogrammed rate, the system notifies a user that a service call is needed. Also, the rates do not need to be preprogrammed, for an adaptive example, the system starts with preprogrammed rates but then tracks actual temperature gains and actual battery discharge and automatically adjusts for the individual differences between different systems by making adjustments to the preprogrammed rates and then any sudden change would prompt the system to inform the user to obtain a service call, but small changes over time (for example, as the tube ages) would not cause the system to inform the user even if the rates were greater than the original preprogrammed rates. In another embodiment, a computed status is calculated to determine how much cooling capacity remains in the module. For example, the difference in temperature between the coolant coming in to the module is compared to the temperature of coolant leaving module, and this difference is integrated over time to determine total cooling performed by the module. This total cooling can be compared to the total cooling ability of the eutectic material and a estimated time to depletion of cooling ability can be determined.

Note that all the above ideas provide for a method of augmenting the capacity of an imaging system. Wherein the method includes plugging a mobile imaging system into a standard outlet, wherein the mobile imaging system has a system battery and a capacitor bank such that the system is able to use more power at peak periods than is provided from the outlet, wherein the mobile imaging system's peak power is P1, and coupling a user removable module to the mobile imaging system such that at least one of the following is provided by the user removable module; an additional cooling capacity; an ability to provide P1 more often; and an additional x-ray power in addition to P1.

In one embodiment, the coolant is in flow communication with a eutectic material which has the capacity to absorb or release heat with little or no change in temperature while in the process of changing from one physical state to another, e.g. solid to liquid or vice versa. The eutectic is a mixture of two or more substances which are miscible as liquids but which have a lower freezing point when combined than either of the two substances separately. The point at which both substances solidify is known as the eutectic point. In one example of the eutectic solution is a solution of a eutectic salt or compound which is formulated to provide good energy storage capability at a given operating temperature. Commercially available "Blue Ice" from the Newell Rubbermaid company of Atlanta Ga., is one example of a suitable eutectic solution. In the eutectic embodiment, besides measuring the temperature for determination of an alarm event, the amount of eutectic material which has undergone a phase change may be tracked. For example, the computed status as set forth above can be used to estimate how much eutectic material is in the solid state and how much is liquid.

Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center.

In use, system 10 is available in the x-ray room, and is used to extend the utility and effectiveness of mobile fluoroscopic equipment. The docking system provides extra electrical energy storage for x-ray power, along with eutectic materials to absorb thermal energy from the x-ray tube, to extend the operating capacity of the mobile equipment. The use of eutectics increases the thermal storage capacity of the x-ray tube cooling system. Typical x-ray tube storage capacity is on the order of 1 to 2 Megajoules. 50 kg of eutectics (e.g., blue ice) can provide a dramatic increase of the thermal storage capacity to something in the area of about 16.7 Megajoules, enough to dissipate 1000 watts for about 4.6 hours. This provides significant added performance capability without the addition of large cumbersome cables along with fluid cooling lines, thus preserving the mobility of the C-arm equipment. Other embodiments provide other amounts of thermal storage capacity. For example, some embodiments provide the ability to dissipate 5 Megajoules or 10 Megajoules. By dissipating a certain energy amount, such as 10 Megajoules, it is meant that that energy is approximately the amount needed to completely phase change the quantity of eutectic material available from solid into liquid.

Additionally, battery energy storage can supply the high surge power requirements for the x-ray system, thus eliminating the need to install special power outlets in the operating suite. Modern day battery systems utilizing Lithium or NiMH technology can provide large energy storage capacity, on the order of 200-800 watts/kg. Thus, a battery weighing about 50 kg can provide 10 kw-40 kw surge power. In cardiac imaging where the x-ray power is pulsed by necessity, the peak power capability is several times greater, for example, 30 kw-100 kw, providing functional utility comparable to fixed room systems. As will be appreciated, embodiments with say 50 kg of eutectics and a 50 kg battery make use of a wheeled module 14 to aid in transport of module 14.

The design of this system provides the capability to dock and undock with ease, to enable "quick change" capacity for the system (hot swap concept). This means that one module 14 could be rapidly exchanged for another module 14 as its capacity becomes exhausted to provide continued service without interrupting medical procedures.

The herein described methods and apparatus provides for extended patient throughput capability, which is one technical effect. They provide extra energy and cooling requirements for long difficult fluoroscopic procedures. They allow increased use of spectral filters for the x-ray beam. Use of spectral filters increases x-ray power demand, but provides patient dose reduction without image quality loss. This is a standard feature on most fixed room systems. Added filtration can cause severe loading conditions for the x-ray tube, requiring higher power requirements and greater cooling demands that the herein described methods and apparatus solve. Fixed room systems transport the heat to a remote location via pipes and cooling systems, and also require large power cables for the peak power demand, since they do not incorporate battery energy buffering.

Dockable modules provide the added utility without significantly interrupting medical procedures, which is another technical effect. The system can be run as a stand-alone device that may or may not require the swappable module. This would mean that the swappable module could either be integrated as a required part of the design or could enhance the stand-alone design. The interesting approaches of these concepts are the simplicity of the concepts that address some concerns of the surgeons. The use of eutectics allows large amounts of heat to be absorbed from the x-ray tube without large temperature increases. The use of an external high-storage capacity battery system also makes large amounts of power available to the x-ray subsystem without the need to increase the electrical mains supply cord and its plug, reducing the need to do special and cumbersome power installations in the clinical suite. The mobility of the dockable module 14 allows for rapid exchanges with another dockable module 14 to allow continued operation when the capacity has been exhausted.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A system for reconstructing an image of an object; said system comprising:
 a mobile imaging system; and
 a user removable module configured to be attached to said mobile imaging system, wherein said mobile imaging system comprises a mobile fluoroscopy system comprising a system battery and a capacitor bank to augment electricity provided by a power cord, and wherein said user removable module comprises a module battery configured to charge said system battery.

2. A system in accordance with claim 1 wherein said mobile imaging system comprises a mobile fluoroscopy system.

3. A system in accordance with claim 1 wherein said user removable module and said mobile fluoroscopy scanner configured to exchange a cooling liquid.

4. A system in accordance with claim 1 wherein said user removable module and said mobile imaging system configured to exchange a cooling liquid.

5. A system in accordance with claim 4 wherein said mobile imaging system comprises a mobile computed tomography scanner.

6. A system in accordance with claim 5 wherein said mobile computed tomography scanner includes a fluoroscopy mode.

7. A system in accordance with claim 1 wherein said mobile imaging system comprises an alert to inform a user that said user removable module should be replaced with another user removable module.

8. A system in accordance with claim 7 wherein said alert is based on at least one of an operating temperature, a eutectic status, and an electrical status.

9. A system in accordance with claim 8 wherein the operating temperature is measured in a cooling liquid, the eutectic status is a computed eutectic status, and the electrical status is the status of a module battery.

10. A system in accordance with claim 1 wherein said mobile imaging system is able to dissipate at least 5 Megajoules of heat.

11. A system in accordance with claim 1 wherein said mobile imaging system is able to dissipate at least 10 Megajoules of heat.

12. A system in accordance with claim 1 wherein said mobile imaging system is able to dissipate at least 16 Megajoules of heat.

13. A system for reconstructing an image of an object; said system comprising:
 a mobile imaging system; and
 a user removable module configured to be attached to said mobile imaging system, wherein said user removable module and said mobile imaging system configured to exchange a cooling liquid, and wherein said user removable module includes a eutectic material.

14. A method of alerting a user of a need for replacing a spent user removable module with a fresh user removable module, said method comprising:
- providing a mobile imaging system associated with the removable module;
- monitoring a temperature of a cooling fluid in a user removable module and/or monitoring a computed status of an amount of eutectic material in a solid state;
- monitoring a charge level of a module battery in the user removable module; and
- alerting the user when at least one of the temperature, the computed status, and the charge level is indicative of a replacement module need.

15. A method in accordance with claim 14 wherein the respective values of the temperature, computed status, and charge level are selected such that at least one half hour of operation is left before shutdown of the a mobile imaging system.

16. A method in accordance with claim 14 further comprising monitoring changes in at least one of the temperature and the charge level and alerting the user to obtain a service call for a mobile imaging system when the monitored changes are abnormal.

* * * * *